United States Patent [19]

Reül et al.

[11] Patent Number: 4,894,232

[45] Date of Patent: Jan. 16, 1990

[54] BASE FOR MUCOSAL AND DENTURE ADHESIVE PASTES, A PROCESS FOR THE PREPARATION THEREOF, AND PASTES HAVING THIS BASE

[75] Inventors: Bernhard Reül, Königstein/Taunus; Walter Petri, Niedernhausen/Taunus, both of Fed. Rep. of Germany

[73] Assignee: Hoechst Aktiengesellschaft, Frankfurt am Main, Fed. Rep. of Germany

[21] Appl. No.: 186,387

[22] Filed: Apr. 26, 1988

[30] Foreign Application Priority Data

Apr. 28, 1987 [DE] Fed. Rep. of Germany ....... 3714074

[51] Int. Cl.$^4$ .......................... A61K 9/06; A61K 6/00
[52] U.S. Cl. .................................... 424/439; 424/485; 424/488
[58] Field of Search ............... 424/439, 488, 484, 485, 424/486

[56] References Cited

U.S. PATENT DOCUMENTS

| | | | |
|---|---|---|---|
| 3,868,260 | 2/1975 | Keegan et al. | 106/35 |
| 3,868,340 | 2/1975 | Keegan et al. | 106/35 X |
| 3,930,871 | 1/1976 | Starace | 106/35 |
| 4,277,364 | 7/1981 | Shasha et al. | 424/488 X |
| 4,661,475 | 4/1987 | Bayerlein et al. | |
| 4,676,976 | 6/1987 | Toba et al. | 424/485 |

*Primary Examiner*—Nancy A. B. Swisher
*Attorney, Agent, or Firm*—Finnegan, Henderson, Farabow, Garrett and Dunner

[57] ABSTRACT

A base for mucosal and denture adhesive pastes, a process for the preparation thereof, and pastes having this base.

A base for mucosal and denture adhesive pastes, pastes having this base, and a process for the preparation thereof, are described.

12 Claims, No Drawings

BASE FOR MUCOSAL AND DENTURE ADHESIVE PASTES, A PROCESS FOR THE PREPARATION THEREOF, AND PASTES HAVING THIS BASE

The invention relates to a base for mucosal pastes and denture adhesive pastes, and to a process for the preparation thereof.

A composition (paste) in which a mucosal ointment base as disclosed in German Patent 1,275,729 (=GB Patent 1,050,967) is used exhibits separation of the liquid phase (=bleeding) after only a short storage time if it contains active ingredients and auxiliaries with surface-active properties.

The liquid separation derives from the impossibility of increasing the viscosity of the internal phase of the paste sufficiently to prevent bleeding. Hence, bleeding cannot be avoided even by increasing the proportionate amount of sodium alginate or low molecular weight cellulose ether, whose colloidal solubility is but limited.

Furthermore, it is impossible to incorporate calcium salts, for example in the form of glycerol adducts which are used to improve the consistency of mucosal and denture adhesive pastes and to increase the adhesion, or as substances influencing the release of active ingredient or as calcium suppliers in modern oral healing pastes, in the described base which contains sodium alginate, because in water sparingly soluble precipitates of calcium alginates occur after application to the mucosa.

These precipitates bring about pronounced solidification of the paste, associated with a considerable reduction in the adhesive effect and duration of adhesion. Pastes of this type do not meet the customary requirements applying to mucosal and denture adhesive pastes.

It has now been found that these disadvantages can be avoided if, in the base described in German Patent 1,275,729, the colloidal solution of low molecular weight cellulose ethers or sodium alginate is replaced by a colloidal solution of the linear, physiologically well tolerated xanthan gum. This substance forms a colloidal solution in the internal phase of the paste, for example in glycerol, and results, even in low concentrations, in significant increases in viscosity.

Hence the invention relates to a base for mucosal and denture adhesive pastes, containing a solid swelling agent which is swellable only in water and is dispersed in a colloidal solution of an organic second swelling agent, which is swellable in water, in a water-soluble, physiologically tolerated organic solvent, wherein the organic second swelling agent is the ionic swelling agent xanthan gum.

The invention also relates to a process for the preparation of a base for mucosal and denture adhesive pastes, which comprises addition of a solid swelling agent which does not swell in the said colloidal solution but is swellable in water to the colloidal solution of xanthan gum in a water-soluble organic physiologically tolerated solvent.

It is advantageous if the swelling agents which are to be dispersed or dissolved are present in finely divided form. Finely divided xanthan gum is obtained by, for example, previous grinding in ethanol. In place of the grinding, the xanthan gum can be dissolved in the water-soluble organic physiologically tolerated solvent, with heating, for example to 50° to 80° C.; the other substances are added after the solution has cooled.

A colloidal solution suitable for taking up the solid swelling agent, which is swellable in water, as base is obtained from xanthan gum and a water-soluble physiologically tolerated organic solvent. Examples of these which can be used are liquid polyhydric alcohols, especially glycerol. The solvents should be anhydrous or contain the minimum amount of water (less than 1%), so that the swelling agent which is not swollen in the paste but is swellable in water does not start to swell in the paste itself.

Suitable swelling agents which are swellable in water and dispersible in the colloidal solution are polysaccharides such as, for example, tragacanth, locust bean gum and galactomannans, especially guaran products such as guar gum (=guaran). It is possible, especially with guaran products, to prepare soft spreadable pastes which rapidly take up moisture, quickly assume the structure of a solid film, and release the pharmaceuticals, which have been incorporated in the paste base where appropriate, slowly to the mucosa at the site of application.

The base according to the invention is smooth, easy to apply and is distinguished by a good and long-lasting adhesiveness. It is suitable as a base for denture adhesive pastes, mocosal and mucosal healing pastes such as wound-covering pastes, antihemorrhoid and vaginal pastes, especially as a base for pastes for treatment of the oral mucosa. Hence the invention also relates to mucosal and denture adhesive pastes having the base according to the invention.

If a paste produced with a base according to the invention is applied to, for example, the oral mucosa, it adheres strongly thereto. The unswollen swelling agent contained in the paste, such as, for example, guaran, immediately takes up, via the water-soluble physiologically tolerated organic solvent, the moisture from the mucosal surface. The film of paste is fixed on the mucosal surface in this way, and solidifies due to the subsequent swelling of the swelling agent.

It was surprising that the increase in viscosity brought about by the ionic polysaccharide xanthan gum is retained even after application to the mucosa and after approach of water, in contrast to an increase in viscosity brought about by cellulose ethers, and is further intensified, where appropriate, depending on the concentration (amount) used. It was not predictable that the polysaccharide in colloidal solution in the internal phase of the paste results in a distinctly improved immediate adhesive effect and duration of adhesion of the paste on the mucosa. This manifestation of the ionic polysaccharide xanthan gum was surprising by comparison with the state of knowledge of the swellability/solubility of polysaccharides in glycerol or water, as well as by comparison with the state of knowledge of the properties of cellulose ethers.

It is possible in principle to incorporate into the base all active substances which can be used topically. Examples of suitable active substances are those of the following groups: antiinflammatory agents, antibiotics, antiseptics, local anesthetics, antihistamines, antimycotics, steroid hormones, antiperiodontosis agents, chemotherapeutics, enzymes and calcium suppliers.

Examples of auxiliaries which can be incorporated are: customary auxiliaries such as, for example, colloidal silica, hydroxyethylcellulose or calcium acetate/ or calcium lactate/glycerol adduct (in German Patent Application P 3,710,177.3 (HOE 87/F 090), calcium lactate/glycerol adduct is proposed for use as auxiliary); furthermore pharmacologically acceptable odor and flavor corrigents such as, for example, saccharin Na or colorants such as, for example, carmine, can be incorporated.

The examples which follow illustrate the invention. For these, the other ingredients are incorporated in the colloidal solution of xanthan gum, with agitation and, where appropriate, under vacuum.

EXAMPLE 1

1 g of wound-covering paste contains:

| | |
|---|---|
| xanthan gum | 5.0 mg |
| guar gum | 225.0 mg |
| glycerol, anhydrous | 770.0 mg |
| | 100.0 mg |

EXAMPLE 2

1 g of denture adhesive paste contains:

| | |
|---|---|
| didecyldimethylammonium chloride | 1.0 mg |
| xanthan gum | 3.0 mg |
| guar gum | 250.0 mg |
| carmine | 0.5 mg |
| glycerol, anhydrous | 745.5 mg |
| | 1000.0 mg |

EXAMPLE 3

1 g of oral healing paste contains:

| | |
|---|---|
| prednisolone 21-acetate (equiv. to 5 mg of prednisolone) | 5.58 mg |
| neomycin.HCl (equiv. to 3.5 mg of base) | 4.37 mg |
| aminoquinuride.HCl, 3.5 H$_2$O | 3.00 mg |
| calcium acetate/glycerol adduct | 175.00 mg |
| xanthan gum | 1.00 mg |
| guar gum | 225.00 mg |
| glycerol, anhydrous | 586.05 mg |
| | 1000.00 mg |

EXAMPLE 4

1 g of oral healing paste contains:

| | |
|---|---|
| didecyldimethylammonium chloride | 2.00 mg |
| lidocaine.HCl.H$_2$O | 5.33 mg |
| calcium lactate/glycerol adduct | 200.00 mg |
| colloidal silica | 1.75 mg |
| xanthan gum | 1.00 mg |
| guar gum | 250.00 mg |
| saccharine Na | 1.00 mg |
| carmine | 0.50 mg |
| glycerol, anhydrous | 538.42 mg |
| | 1000.00 mg |

EXAMPLE 5

1 g of oral healing paste contains:

| | |
|---|---|
| calcium glycerophosphate.H$_2$O | 125.83 mg |

-continued

| | |
|---|---|
| xanthan gum | 2.00 mg |
| guar gum | 200.00 mg |
| saccharine Na | 0.50 mg |
| carmine | 0.50 mg |
| glycerol, anhydrous | 671.17 mg |
| | 1000.00 mg |

EXAMPLE 6

1 g of antihemorrhoid paste contains:

| | |
|---|---|
| fluorometholone | 0.20 mg |
| neomycin.HCl | 2.00 mg |
| aminoquinuride.HCl. 3,5 H$_2$O | 3.00 mg |
| pheniramine.HCl | 11.52 mg |
| xanthan gum | 2.00 mg |
| guar gum | 250.00 mg |
| glycerol, anhydrous | 731.28 mg |
| | 1000.00 mg |

EXAMPLE 7

1 g of antihemorrhoid paste contains:

| | |
|---|---|
| chlorhexidine.2HCl | 2.00 mg |
| lidocaine.HCl.H$_2$O | 5.33 mg |
| allantoin | 5.00 mg |
| dexpanthenol | 5.00 mg |
| azulene | 2.00 mg |
| xanthan gum | 3.00 mg |
| guar gum | 225.00 mg |
| glycerol, anhydrous | 752.67 mg |
| | 1000.00 mg |

EXAMPLE 8

1 g of vaginal paste contains:

| | |
|---|---|
| ciclopirox | 7.71 mg |
| xanthan gum | 3.00 mg |
| guar gum | 100.00 mg |
| glycerol, anhydrous | 889.29 mg |
| | 1000.00 mg |

EXAMPLE 9

1 g of vaginal paste contains:

| | |
|---|---|
| estriol | 0.01 mg |
| benzalkonium chloride | 2.00 mg |
| xanthan gum | 2.50 mg |
| guar gum | 200.00 mg |
| glycerol, anhydrous | 795.49 mg |
| | 1000.00 mg |

EXAMPLE 10

1 g of periodontosis healing paste contains:

| | |
|---|---|
| dicalcium hydrogen phosphate.2H$_2$O | 100.00 mg |
| soduim monohydrogen phosphate.2H$_2$O | 5.00 mg |
| magnesium ammonium phosphate.6H$_2$O | 10.00 mg |
| sodium fluoride | 3.65 mg |

| -continued | |
|---|---|
| (equiv. to 2 mg of fluorine) | |
| xanthan gum | 1.00 mg |
| guar gum | 200.00 mg |
| glycerol, anhydrous | 680.35 mg |
| | 1000.00 mg |

We claim:

1. A base for mucosal and denture adhesive pastes comprising, a solid swelling agent which is swellable only in water and is dispersed in a colloidal solution of an organic second swelling agent in a water-soluble, physiologically tolerated organic solvent, wherein the organic second swelling agent is swellable in water and is an ionic swelling agent xanthum gum.

2. A mucosal paste comprising a base as claimed in claim 1, and an active substance which can be topically applied, with or without customary auxiliaries.

3. A mucosal paste comprising a base as claimed in claim 1, customary auxiliaries and at least one active substance selected from the group consisting of antiinflammatory agents, antibiotics, antiseptics, local anesthetics, antihistamines, antimycotics, steroid hormones, antiperidontosis agents, chemotherapeutics, enzymes and calcium suppliers.

4. A mucosal paste for treating oral mucosa, comprising a base as claimed in claim 1, customary auxiliaries and at least one active substance selected from the group consisting of antiinflammatory agents, antibiotics, antiseptics, local anesthetics, antiperidontosis agents and calcium suppliers.

5. A denture adhesive paste comprising a base as claimed in claim 1, and an active substance which can be topically applied, with or without customary auxiliaries.

6. The base as claimed in claim 1, wherein the water-soluble, physiologically tolerated organic solvent is anhydrous.

7. The base as claimed in claim 1, wherein the water-soluble, physiologically tolerated organic solvent is a liquid polyhydric alcohol.

8. The base as claimed in claim 7, wherein the polyhydric alcohol is glycerol.

9. A process for the preparation of a base for mucusal and denture adhesive pastes, which comprises adding a solid swelling agent, which does not swell in a colloidal solution but is swellable in water, to the colloidal solution of xanthan gum in a water-soluble organic physiologically tolerated solvent.

10. The process as claimed in claim 9, wherein the water-soluble organic physiologically tolerated solvent is anhydrous.

11. The process as claimed claim 9, wherein the water-soluble organic physiologically tolerated solvent is a liquid polyhydric alcohol.

12. The process as claimed in claim 11, wherein the polyhydric alcohol is glycerol.

* * * * *